United States Patent
Dykaar et al.

(10) Patent No.: US 6,891,926 B1
(45) Date of Patent: May 10, 2005

(54) FIBER BUNDLES FOR X-RAY IMAGING

(75) Inventors: Douglas Raymond Dykaar, Waterloo (CA); Colin J. Flood, Kitchener (CA)

(73) Assignee: Dalsa, Inc., Waterloo (CA)

( * ) Notice: Subject to any disclaimer, the term of this patent is extended or adjusted under 35 U.S.C. 154(b) by 151 days.

(21) Appl. No.: 09/924,718

(22) Filed: Aug. 9, 2001

Related U.S. Application Data

(60) Provisional application No. 60/223,965, filed on Aug. 9, 2000.

(51) Int. Cl.[7] .................................................. H05G 1/64
(52) U.S. Cl. ....................... 378/98.8; 385/115; 385/116; 250/370.09; 250/370.11
(58) Field of Search ............................... 378/98.3, 98.8; 385/115, 116; 250/370.09, 370.11, 390, 366–368

(56) References Cited

U.S. PATENT DOCUMENTS

| | | | |
|---|---|---|---|
| 3,874,783 A | | 4/1975 | Cole ........................... 385/115 |
| 4,099,833 A | | 7/1978 | Tosswill ....................... 385/43 |
| 4,139,261 A | | 2/1979 | Hilsum ........................ 385/120 |
| 4,179,100 A | | 12/1979 | Sashin et al. .......... 250/370.09 |
| 4,344,668 A | | 8/1982 | Gunther et al. ............. 385/120 |
| 4,696,022 A | | 9/1987 | Sashin et al. ................. 385/41 |
| 4,946,238 A | | 8/1990 | Sashin et al. ............... 385/116 |
| 5,303,373 A | * | 4/1994 | Harootian, Jr. ............. 385/115 |
| 5,381,502 A | | 1/1995 | Veligdan ..................... 385/115 |
| 5,550,380 A | * | 8/1996 | Sugawara et al. ..... 250/370.11 |
| 5,600,751 A | | 2/1997 | Peli ............................ 385/116 |
| 5,640,018 A | * | 6/1997 | Suzuki et al. ............... 250/368 |
| 5,684,906 A | | 11/1997 | Sugawara ................... 385/120 |
| 5,694,448 A | | 12/1997 | Morcom .................... 378/98.8 |
| 5,784,429 A | | 7/1998 | Arai ............................. 378/38 |
| 5,784,434 A | | 7/1998 | Shieh ......................... 378/191 |
| 5,808,729 A | | 9/1998 | Sugawara et al. ............. 356/71 |
| 5,894,129 A | | 4/1999 | Pool ...................... 250/370.09 |
| 5,903,694 A | | 5/1999 | Sugawara ................... 385/121 |
| 5,923,806 A | | 7/1999 | Sugawara ................... 385/121 |
| 6,031,954 A | | 2/2000 | Higuchi ...................... 385/120 |
| 6,479,827 B1 | * | 11/2002 | Hamamoto et al. .... 250/370.11 |

* cited by examiner

*Primary Examiner*—Edward J. Glick
*Assistant Examiner*—Courtney Thomas
(74) *Attorney, Agent, or Firm*—Millen, White, Zelano, Branigan, P.C.

(57) ABSTRACT

An apparatus includes a sensor and a bundle of optical fibers. The bundle of optical fibers has a first end and a second end. The bundle of optical fibers at the first end extends in a first fiber direction and defines a first section plane that is normal to the first fiber direction. The first end defines a first end plane that is obliquely oriented with respect to the first section plane. The bundle of optical fibers at the second end extends in a second fiber direction and defines a second section plane that is normal to the second fiber direction. The second end defines a second end plane that is obliquely oriented with respect to the second section plane. The sensor is disposed in a confronting relation with the second end.

31 Claims, 4 Drawing Sheets

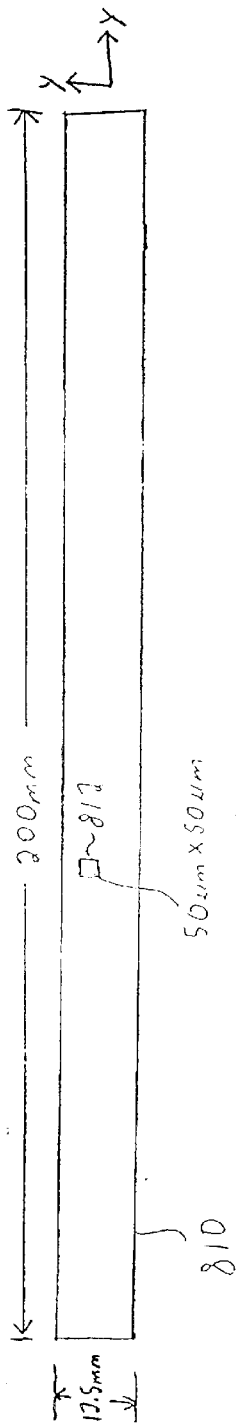
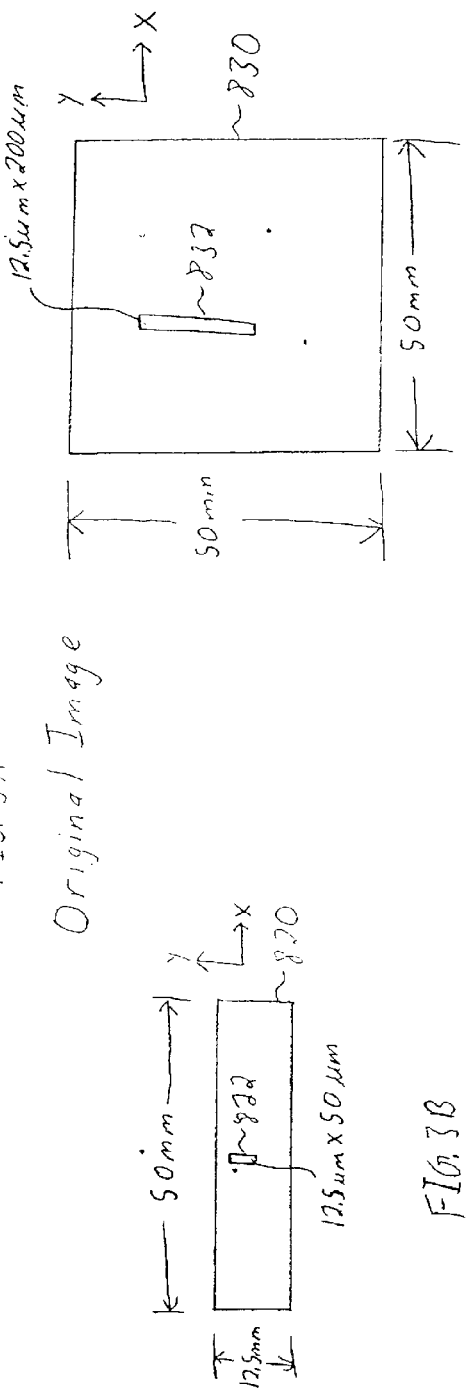

FIBER BUNDLES FOR X-RAY IMAGING

BACKGROUND OF THE INVENTION

The priority benefit of the Aug. 9, 2000 filing date of provisional application Ser. No. 60/223,965 is hereby claimed.

FIELD OF THE INVENTION

The present invention relates to an imaging device as typically used for dental imaging. In particular, the invention relates to use of a combination of a CCD imaging sensor with a radiation scintillator and an interadjacent fiber optic bundle.

DESCRIPTION OF RELATED ART

The use of self-scanning photodiode arrays, such as CCD sensors, in the area of medical, industrial, and other environments is well known. In particular, time delay and integrate (TDI) CCD sensors have been used in the area of dental imaging. For example, in U.S. Pat. No. 5,784,429 (Arai), a dental panoramic imaging apparatus uses a scintillator which converts radiations impinging thereon into visible light, an optical fiber plate which guides an image of the scintillator, and a TDI CCD device for converting the image guided by the optical fiber into electric signals. The sensors in turn convert the light into electric signals to be stored in a memory or used to display the image. However, the Arai patent does not solve the problem of fitting a relatively large image onto a smaller TDI CCD sensor. Arai suggests using more than one sensor if necessary. Use of more than one sensor would create undesirable edge or seam artifacts within the image. Furthermore, in the case of TDI, problems with alignment and clocking of the edge pixel may be insurmountable.

To alleviate this problem with edge pixels, another solution, for example in U.S. Pat. Nos. 4,696,022 (Sashin) and 4,946,238 (Sashin) has been to affix the scintillator to a fiber optic bundle which has been cut at an angle relative to the direction of the fibers and to the plane of the CCD sensor, where the direction of the fibers and the CCD sensor plane are perpendicular. By using fibers with an angled end face, the image introduced into the fibers at the scintillator end is reduced so that the sensor can be smaller in one dimension (length) than the scintillator.

A limitation with this approach is that by reducing the size of the sensor, the sizes of individual pixels and their charge storage well capacities are also reduced. The full well capacity establishes the maximum dynamic range of the captured image. The attempt to maintain both the required resolution and dynamic range in a shortened sensor is in conflict. In general, full well capacity is proportional to pixel area. If, for example, the reduction in length is by a factor of four, a 50 $\mu$m pixel size is reduced (in one dimension) from 50 $\mu$m to 12.5 $\mu$m, reducing the full well capacity by a factor of four (e.g. from $1.5 \times 10^6$ to $0.375 \times 10^6$ electrons). It is desired to achieve adequate resolution and to regain the full well capacity. For example, the image impinging on the TDI CCD sensor might regain its original surface area in a way that does not require butting sensors.

SUMMARY OF THE INVENTION

It is an object of the invention to overcome limitations in the prior art. It is a further object of the invention to morph an image in a first format at a first end of a fiber bundle into an image in a second format at a second end of the fiber bundle.

These and other objects are achieved in an apparatus that includes a sensor and a bundle of optical fibers. The bundle of optical fibers has a first end and a second end. The bundle of optical fibers at the first end extends in a first fiber direction and defines a first section plane that is normal to the first fiber direction. The first end defines a first end plane that is obliquely oriented with respect to the first section plane. The bundle of optical fibers at the second end extends in a second fiber direction and defines a second section plane that is normal to the second fiber direction. The second end defines a second end plane that is obliquely oriented with respect to the second section plane. The sensor is disposed in a confronting relation with the second end.

These an other objects are also achieved in an apparatus that includes a sensor and a bundle of optical fibers. The bundle of optical fibers is capable of morphing a first format at a first end into a second format at a second end. The first end is non-normal to a first fiber direction at the first end. The second end is non-normal to a second fiber direction at the second end. The sensor is disposed in a confronting relation with the second end.

These an other objects are further achieved in an apparatus that includes a radiation generator for generating incident radiation. The apparatus further includes a scintillator disposed in a confronting relation with the radiation generator and formed of a material capable of transforming the incident radiation into a visible light image. The apparatus also includes a fiber optic bundle having a first end disposed in a confronting relation with the scintillator and finished along a plane oriented with respect to a first end fiber direction to compress the visible light image in a first image direction, the fiber optic bundle also having a second end finished along another plane oriented with respect to a second fiber direction to expand the visible light image in a second image direction, and the fiber optic bundle further having a transmitting region disposed between the first end and the second end. The apparatus also includes a time delay and integrate sensor disposed in confronting relation with the second end. The apparatus further includes a display coupled to the time delay and integrate sensor.

These and other objects are achieved in an alternative embodiment in which a method for imaging an object includes the steps of compressing the visible light image in a first image direction, expanding the visible light image in a second image direction, and converting the visible light image to an electronic image.

BRIEF DESCRIPTION OF DRAWINGS

The invention will be described in detail in the following description of preferred embodiments with reference to the following figures wherein:

FIG. 3A is a diagram of original image;

FIG. 3B is a diagram of compressed image;

FIG. 3C is a diagram of expanded image; and

DETAILED DESCRIPTION OF PREFERRED EMBODIMENTS

Figure 1:
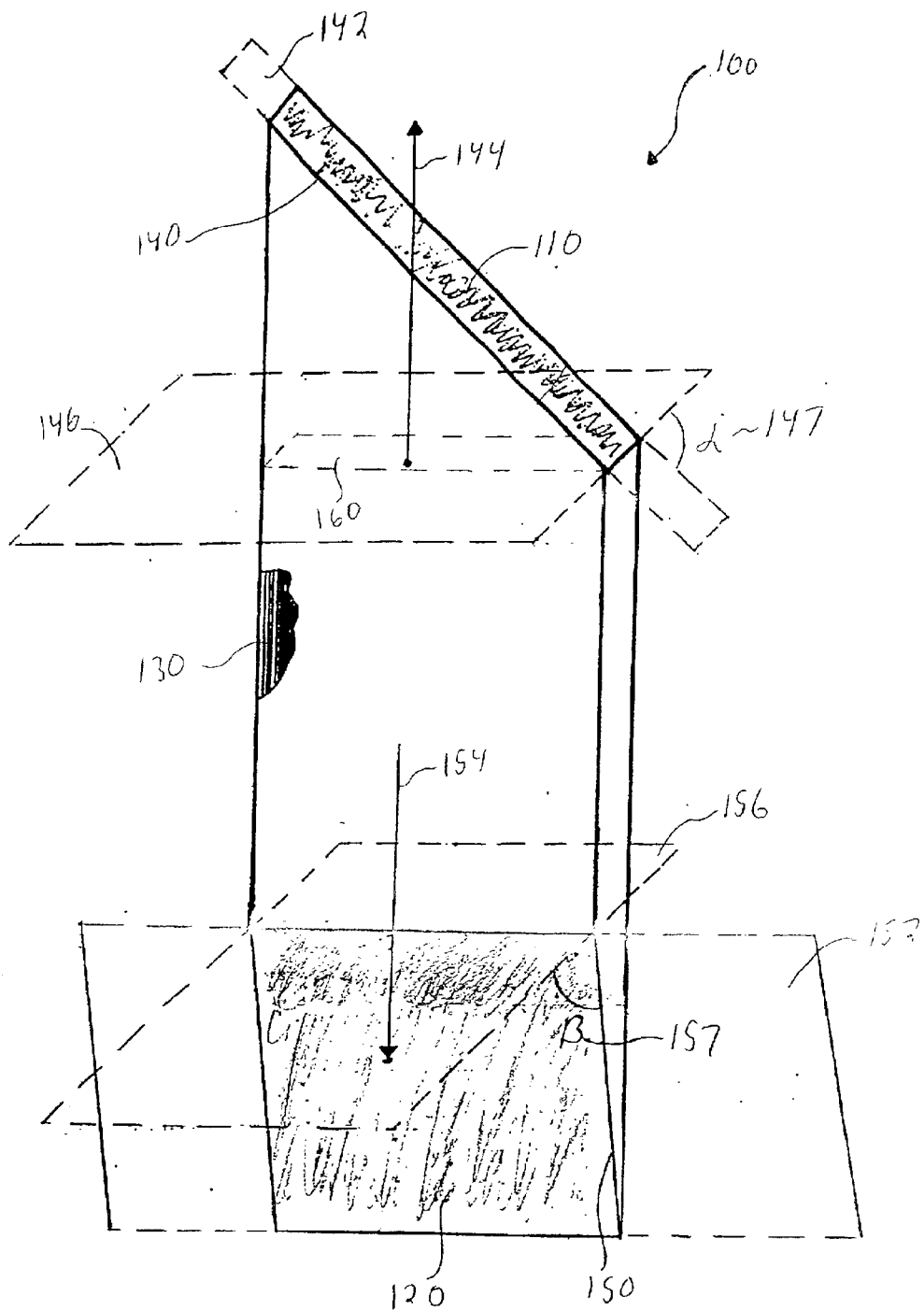
FIG. 1 is a diagram of the preferred embodiment of imager.

In FIG. 1, imager 100 includes scintillator 110, imaging sensor 120, and bundle of optical fibers 130 disposed therebetween (i.e., interadjacent). Bundle of optical fibers 130 extends between first (receiving) end face 140 and second (discharging) end face 150. Receiving end face 140 defines receiving end plane 142. All fibers in bundle of optical fibers 130 at receiving end face 140 are co-parallel to first fiber direction 144. First fiber direction 144 defines receiving end section plane 146 as a plane that is normal to first fiber direction 144 and intersects receiving end face 140 at a location closest to imaging sensor 120. Receiving end plane 142 defines an oblique angle α 147 with receiving end section plane 146.

Discharging end face 150 defines discharging end plane 152. All fibers in bundle of optical fibers 130 at discharging end face 150 are co-parallel to second fiber direction 154. Second fiber direction 154 defines discharging end section plane 156 as a plane that is normal to second fiber direction 154 and intersects discharging end face 150. Discharging end plane 152 defines an oblique angle β 157 with discharging end section plane 156.

In one embodiment, first fiber direction 144 is co-parallel with second fiber direction 154. Bundle of optical fibers 130 includes plural straight fibers all co-parallel with first or second fiber direction 144 or 154. A diameter of an individual fiber is typically less than 25 μm, preferably less than 10 μm (e.g., 6 μm to 8 μm). All fibers are bound together.

In an alternative embodiment, first fiber direction 144 is not co-parallel with second fiber direction 154. Bundle of optical fibers 130 includes plural fibers that are straight and co-parallel with first fiber direction 144 at the receiving end and plural fibers that are straight and co-parallel with second fiber direction 154 at the discharging end, but the fibers bend (around one or more curves) between the receiving and discharging end.

Figure 2:
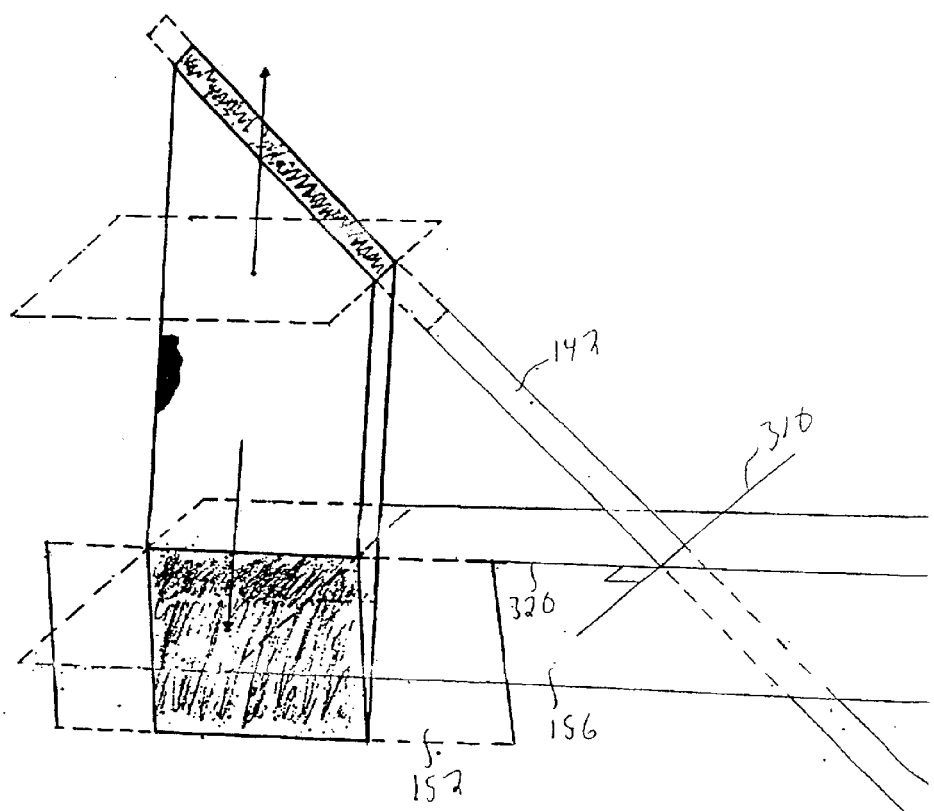
FIG. 2 is a diagram of the planar detail of imager.
Figure 4:
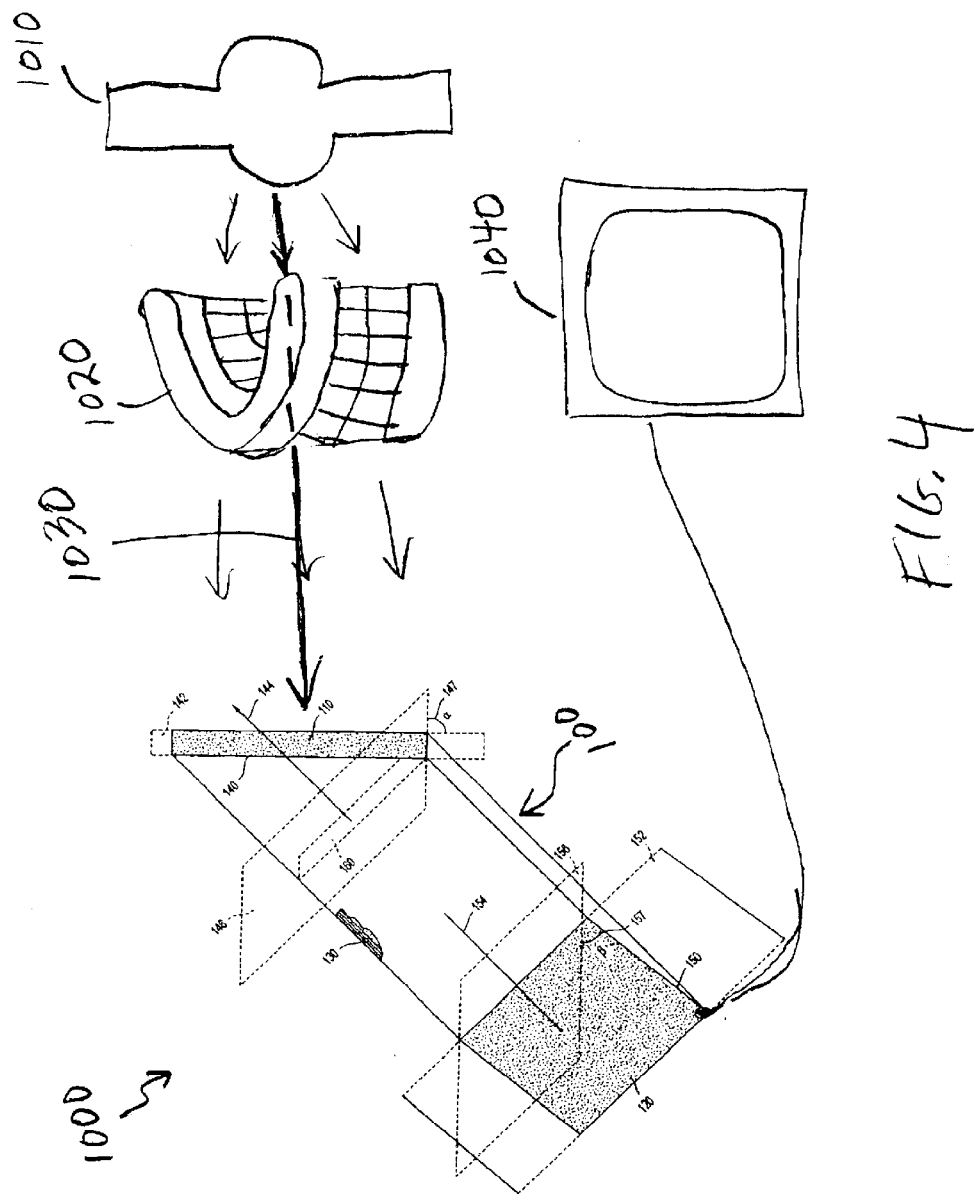
FIG. 4 is a schematic diagram of an application using an embodiment of the invention.

In FIG. 2, receiving end plane 142 intersects discharging end section plane 156 at first intersection line 310. Discharging end plane 152 intersects discharging end section plane 156 at second intersection line 320. First and second intersection lines 310, 320 are transverse to each other and in the plane of discharging end section plane 156. Preferably, first and second intersection lines 310, 320 are perpendicular to each other.

In operation, incoming radiations or other forms of radiation impinge scintillator 110. Scintillator 110 converts the radiation into visible light. In this context, the term "visible light" refers to light within the spectral response of the imager 100. For a silicon-based CCD sensor, the spectral response extends into both the ultraviolet and the near infrared portions of the spectrum. Therefore, the scintillator 110 converts the radiation into wavelengths more suited to the transmission properties of the fiber and to the spectral response of the image sensor. The term "visible light" in this context should not be construed as limited to light within the spectral range that is visible to humans.

Scintillator 110 is affixed to receiving end face 140 of bundle of optical fibers 130. Receiving end face 140 is the incident end of fiber optic bundle 130 which transports the visible light from receiving end face 140 to discharging end face 150. Sensor 120, preferably a time-delay and integrate (TDI) CCD sensor, is affixed to discharging end face 150 of bundle of optical fibers 130. Sensor 120 converts the visible light from bundle of optical fiber 130 into electrical signals, which may be used to display the image or may be put to some other use.

In FIG. 1, image section 160 is a section of bundle of optical fibers 130 in receiving end section plane 146. Persons of ordinary skill in the art in light of these teachings will appreciate that image section 160 might be defined to be any equally sized section of bundle of optical fibers 130 normal to the local fiber direction that is located between receiving end face 140 and discharging end face 150. The area of scintillator 110 is greater than the area of image section 160. As a result of the angle between receiving end plane 142 and receiving end section plane 146, the visible light impinging on receiving end plane 142 from scintillator 110 is compressed to fit into image section 160.

At discharging end face 150, the visible light is first expanded in a direction transverse to the previous compression and then transmitted to sensor 120. The image expansion is a result of the angle between discharging end plane 152 and discharging end section plane 156.

In FIG. 3A, in an exemplary embodiment, original image 810 is 200 mm by 12.5 mm and contains a plurality of pixels 812, each of which are 50 μm by 50 μm. In this example, there are 4000 pixels in the x-direction and 250 pixels in the y-direction. Original image 810 impinges on receiving end plane 142 from scintillator 110. Original image 810 and accordingly, each pixel 812, are compressed in the x-direction as original image 810 is transmitted from scintillator 110 through receiving end face 140.

In this example, the image is compressed in the x-direction from 200 mm to 50 mm and the pixels are compressed from 50 μm to 12.5 μm. In FIG. 3B, compressed image 820 of this example is 50 mm (compressed) by 12.5 mm (uncompressed) and contains a plurality of pixels 822, which are now 12.5 μm (compressed) by 50 μm (uncompressed). Compressed image 820 and pixel 822 are expanded in the y-direction as compressed image 820 is transmitted through discharging end face 150. In FIG. 3C, expanded image 830 of this example is 50 mm (compressed) by 50 mm (expanded) and contains a plurality of pixels 832, which are now 12.5 μm (compressed) by 200 μm (expanded). Expanded image 830 at discharge end face 150 impinges on sensor 120. It should be noted that the expansion in the y-direction exactly compensates for the compression in the x-direction so that discharge end pixel 832 has the same area as received end pixel 812.

The angle between receiving end plane 142 and receiving end section plane 146 morphs original pixels 812 from their initial size, for example 50 μm by 50 μm in FIG. 3A, into compressed pixels 822 as the light reaches image section 160. For instance, incoming square pixels 812 are morphed into compressed 12.5 μm by 50 μm rectangular pixels 822 in FIG. 3B. Likewise, the angle between discharging end plane 152 and discharging end section plane 156 morphs compressed pixels 822 into expanded pixels 832 at discharging end face 150 and from there into sensor 120. For example, in FIG. 3C, compressed pixels 822 become expanded pixels 832 that are 12.5 μm by 200 μm rectangular pixels. Persons skilled in this art will appreciate in light of these teachings that the original image format at receiving end face 140 (200 mm by 12.5 mm) is morphed into a compressed image format through image section 160 (50 mm by 12.5 mm), and from there morphed into an expanded image format at discharging end face 150 (50 mm by 50 mm).

Compression of original image 810 into compressed image 820 enables one sensor 120 to image light from scintillator 110 without requiring multiple sensors 120 to be abutted. At the same time, the area of compressed pixel 822 is reduced with respect to original pixel 812 by the same compression factor. Even though subsequent expansion of compressed image 820 into expanded image 830 increases the size of expanded image 830, expanded image 830 still fits well within the format of a single sensor (i.e., sensor 120). At the same time, the area of expanded pixel 832 is enlarged with respect to compressed pixel 822 by the same expansion factor. When the compression ratio equals the expansion ratio, the area of expanded pixel 832 is equal to the area of original pixel 812, but the shapes of original pixel 812 and expanded pixel 832 are different.

Sensor 120 includes an array of photo detectors, typically photo gates, photo diodes or pinned photo diodes. The charge storage capacity of a pixel is proportional to the area of the photo detector in the pixel, all other factors being equal. In the example discussed above, the area of expanded pixel 832 is maintained equal to the area of original pixel 812, but the shape is different. In the example discussed above, the charge storage capacity of a photo detector disposed to detect light at expanded pixel 832 is the same as the charge storage capacity that would characterize a photo detector disposed to detect light from original pixel 812. Both pixels have the same area although both pixels have different shapes.

For example, when the reduction in length between receiving end face 140 and image section 160 is a factor of four, as is shown by FIGS. 3A and 3B, the pixel is reduced (in one dimension) from 50 μm to 12.5 μm. Uncompensated, this reduction would lead to a decrease in the full well capacity of corresponding pixels in sensor 120 by a factor of four (e.g., from $1.5 \times 10^6$ to $0.374 \times 10^6$ electrons). A loss in the amount of charge able to be collected and held in a storage well of a pixel in sensor 120 corresponds to a loss in dynamic range of a signal that can be sensed by sensor 120. This loss in dynamic range of a signal that can be sensed will adversely affect the quality of the resulting image output from sensor 120.

In this example, when the enlargement in length between imaging section 160 and discharging end face 150 is a factor of four, as is shown by FIGS. 3B and 3C, the pixel is enlarged (in another dimension) from 50 μm to 200 μm. This enlargement effectively maintains the full well capacity of pixels in sensor 120. Restoring the area of original pixel 812 at the discharging end face 150 as expanded pixel 832 enables the amount of charge able to be collected and held in a storage well of a pixel in sensor 120 to be equal the charge that could be collected and stored by a like sensor disposed to detect light from original pixel 812. Therefore, restoring the area of original pixel 812 at discharging end face 150 as expanded pixel 832 enables the dynamic range of a signal detectable by sensor 120 to be equal the dynamic range that could be detected by a like sensor disposed to detect light from original pixel 812.

In effect, the photosensitive area of the new sensor can be the same as a grouping of butted sensors, but the long length has been converted into increased width. As seen in FIG. 3C, the pixel is now 12.5 μm by 200 μm and has the same area as the original 50 μm by 50 μm pixel.

Depending on the application, the discharging end pixel size may be adjusted to overcompensate, undercompensate, or exactly restore any loss in pixel size occasioned by the compression. Loss of pixel size due to compression is directly related to the magnitude of the angle between receiving end plane 142 and receiving end section plane 146. The recovery of the dynamic range, or lack thereof, is directly related to the magnitude of the angle between discharging end plane 152 and discharging end section plane 156. In a preferred embodiment, the ratio between the recovery of the pixel size and the original loss is 1:1. When the compression is a 4:1 ratio, the recovery is preferably a 1:4 ratio.

However, in an alternative embodiment, both the compression and expansion ratios may be adjusted as required by the situation. Although the 4:1/1:4 compression/expansion ratio is preferred in some instances to morph large aspect ratio areas into large substantially square TDI sensors, in general, larger ratios (m:1 and 1:n, where m or n is much different from unity) are limited only by transmission properties at the fiber interface, i.e., losses due to reflection, possible crosstalk issues, etc. The preferred ratio, with n=m=4, is considered to be a relatively large ratio with a measurable transmission loss. There is no such limit for smaller ratios, with n and m closer to unity. However, the utility of the imager 100, as taught in this disclosure, is obviously negated at n=m=1. Although there may be an optimal ratio with respect to transmission properties associated with Brewster's angle and the corresponding ratios, it is practical for the ratio to be anywhere from 1<m,n<=10, with a more preferable range of 1.5<=m,n<=4.

Both the compression and expansion ratios may be adjusted as required by the situation. For instance, the angle between receiving end plane 142 and receiving end section plane 146 may be adjusted such that the compression ratio could be anywhere from 6:1 to 2:1. In other embodiments, the compression ratio could be anywhere from 8:1 to 1.5 to 1, depending on the magnitude of the angle between receiving end plane 142 and receiving end section plane 146.

Likewise, the amount of recovery of the dynamic range is affected by the magnitude of the angle between discharging end plane 152 and discharging end section plane 156. While a 1:4 expansion ratio may exist in a preferred embodiment, in an alternative embodiment, the angle between discharging end plane 152 and discharging end section plane 156 may be adjusted such that the expansion ratio could be anywhere from 1:2 to 1:6. In other embodiments, the expansion ratio could be anywhere from 1:1.5 to 1:8, depending on the magnitude of the angle between discharging end plane 152 and discharging end section plane 156.

In a preferred embodiment, sensor 120 is a time delay and integrate (hereinafter TDI) sensor. In this example, sensor 120 includes an array of photo detectors organized as 4000 columns by 250 elements in each column. As an image conjugate moves across the sensor in the column direction, the sensor is clocked synchronously to transport the accumulating charge down the columns. A single pixel will first be sensed by a first photo detector at the top of a column. As the image conjugate moves the pixel to the next photo detector, the clocking system clocks the sensor to move the accumulating photo charge to the next photo detector in the column in order to continue accumulating photo charge corresponding to the intensity of light in that pixel. This process is repeated until the photo charge is accumulated from all 250 photo detector elements in a column. Then the accumulated charge is transferred to a readout register and transferred out of sensor 120.

An exemplary use of imager 100 is in a dental imaging system 1000. During the imaging processes, a rotary mechanism rotates and translates both a radiation source 1010 and imager 100 around the object 1020 (e.g., a human head—or more specifically, teeth—along a dental plane) to be imaged. The rotation and translation of a line 1030 between imager 100 and the radiation source 1010, as well as the TDI scan rate of sensor 120 of imager 100 are controlled in order to compensate for the non-semicircular shape of the dental line of the human jaw. The output of TDI sensor 120 is coupled to display 1040 to view the dental image.

Having described preferred embodiments of a novel imager having a CCD sensor and a method for using the imager (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as defined by the appended claims.

Having thus described the invention with the details and particularity required by the patent laws, what is claimed and desired protected by letters patent is at forth in the appended claims.

What is claimed is:

1. An apparatus, comprising a sensor and a bundle of optical fibers having first and second ends; wherein:

the bundle of optical fibers at the first end extends in a first fiber direction and defines a first section plane that is normal to the first fiber direction;

the first end defines a first end plane that is obliquely oriented with respect to the first section plane;

the bundle of optical fibers at the second end extends in a second fiber direction and defines a second section plane that is normal to the second fiber direction;

the second end defines a second end plane that is obliquely oriented with respect to the second section plane;

the first and second end planes intersect at an intersection line;

an orthogonal plane is defined orthogonal to a fiber direction of the bundle of optical fibers;

the orthogonal plane intersects the intersection line at only one point; and the sensor is disposed in a confronting relation with the second end.

2. The apparatus of claim 1, wherein the first fiber direction and the second fiber direction are co-parallel.

3. The apparatus of claim 1, wherein the sensor is a time delay and integrate sensor.

4. The apparatus of claim 1, further comprising a scintillator disposed in a confronting relation with the first end.

5. The apparatus of claim 4, wherein the first fiber direction and the second fiber direction are co-parallel.

6. The apparatus of claim 4, wherein the sensor is a time delay and integrate sensor.

7. The apparatus of claim 1, further comprising a radiation source disposed in a confronting relation with the first end of the bundle of optical fibers.

8. The apparatus of claim 7, further comprising a scintillator disposed in a confronting relation with the first end of the bundle of optical fibers, wherein the radiation source is an x-ray source.

9. The apparatus of claim 7, wherein:

the sensor is a time delay and integrate sensor with a sensor control; and the sensor control is capable of operating the sensor to image an article disposed between the radiation source and the first end of the bundle of optical fibers that is moving relative and transverse to a radiation axis between the radiation source and the first end of the bundle of optical fibers.

10. The apparatus of claim 9, further comprising a scintillator disposed in a confronting relation with the first end of the bundle of optical fibers, wherein the radiation source is an x-ray source.

11. The apparatus of claim 9, wherein the time delay and integrate sensor is a CCD photodiode array.

12. An apparatus comprising a sensor and a bundle of optical fibers having first and second ends, wherein:

the bundle of optical fibers at the first end extends in a first fiber direction and defines a first section plane that is normal to the first fiber direction;

the first end defines a first end plane that is obliquely oriented with respect to the first section plane;

the bundle of optical fibers at the second end extends in a second fiber direction and defines a second section plane that is normal to the second fiber direction;

the second end defines a second end plane that is obliquely oriented with respect to the second section plane;

the sensor is disposed in a confronting relation with the second end;

the bundle of optical fibers is shaped to define a first angle between the first end plane and the first section plane;

the bundle of optical fibers is shaped to further define a second angle between the second end plane and the second section plane;

the first angle renders the apparatus capable of compressing in a first image direction an optical image impinging on the first end into an optical image in the bundle of optical fibers at the first section plane;

the second angle renders the apparatus capable of expanding in a second image direction an optical image from the bundle of optical fibers at the second section plane into an optical image emitting from the second end; and the second image direction is transverse to the first image direction.

13. The apparatus of claim 12, wherein the compression in the first image direction is between 10:1 and m:1, where 1<m<10.

14. The apparatus of claim 12, wherein the compression in the first image direction is between 4:1 and 1.5:1.

15. The apparatus of claim 12, wherein the compression in the first image direction is 4:1.

16. The apparatus of claim 12, wherein the expansion in the second image direction is between 1:10 and 1:n, where 1<n<10.

17. The apparatus of claim 12, wherein the expansion in the second image direction is between 1:4 and 1:1.5.

18. The apparatus of claim 12, wherein the expansion in the second image direction is 1:4.

19. An apparatus comprising a sensor and a bundle of optical fibers having first and second ends, wherein:

the bundle of optical fibers at the first end extends in a first fiber direction and defines a first section plane that is normal to the first fiber direction;

the first end defines a first end plane that is obliquely oriented with respect to the first section plane;

the bundle of optical fibers at the second end extends in a second fiber direction and defines a second section plane that is normal to the second fiber direction;

the second end defines a second end plane that is obliquely oriented with respect to the second section plane;

the sensor is disposed in a confronting relation with the second end;

the first end plane intersects the second section plane at a first line;

the second end plane intersects the second section plane at a second line; and the first line is transverse to the second line.

20. The apparatus of claim 19, wherein
the first line is perpendicular to the second line.

21. An apparatus of claim 1 comprising a sensor and a bundle of optical fibers having first and second ends, wherein:

the bundle of optical fibers at the first end extends in a first fiber direction and defines a first section plane that is normal to the first fiber direction;

the first end defines a first end plane that is obliguely oriented with respect to the first section plane;

the bundle of optical fibers at the second end extends in a second fiber direction and defines a second section plane that is normal to the second fiber direction;

the second end defines a second end plane that is obliquely oriented with respect to the second section plane;

the sensor is disposed in a confronting relation with the second end; and the bundle of optical fibers is capable of morphing a first rectangular format image at the first end into a second rectangular format image at the second end, the first rectangular format image having an aspect ratio different than an aspect ratio of the second rectangular format image.

22. The apparatus of claim 21, wherein the first end defines a first end plane and the second end defines a second end plane which is obliquely oriented with respect to the first end plane.

23. The apparatus of claim 21, wherein the sensor is a time delay and integrate sensor.

24. The apparatus of claim 21, further comprising a scintillator disposed in a confronting relation with the first end.

25. The apparatus of claim 24, wherein the sensor is a time delay and integrate sensor.

26. The apparatus of claim 25, wherein:

the first end is non-normal to a fiber direction at the first end; and the second end is non-normal to a fiber direction at the second end.

27. The apparatus of claim 25, wherein the first end is defined by a first end plane and the second end is defined by a second end plane which is obliquely oriented with respect to the first end plane.

28. An apparatus comprising a sensor and a bundle of optical fibers having first and second ends, wherein:

the bundle of optical fibers at the first end extends in a first fiber direction and defines a first section plane that is normal to the first fiber direction;

the first end defines a first end plane that is obliquely oriented with respect to the first section plane;

the bundle of optical fibers at the second end extends in a second fiber direction and defines a second section plane that is normal to the second fiber direction;

the second end defines a second end plane that is obliguely oriented with respect to the second section plane;

the sensor is disposed in a confronting relation with the second end; and the bundle of optical fibers is capable of morphing a first format at the first end into a second format at the second end, characterized in that when a compression ratio equals an expansion ratio, the area of the first format equals the area of the second format, but shape of the first format and the shape of the second format are different.

29. An apparatus comprising:

a radiation generator for generating incident radiation;

a scintillator disposed in a confronting relation with the radiation generator and formed of a material capable of transforming the incident radiation into a visible light image;

a fiber optic bundle having a first end disposed in a confronting relation with the scintillator and finished along a plane oriented with respect to a first end fiber direction to compress the visible light image in a first image direction, the fiber optic bundle also having a second end finished along another plane oriented with respect to a second end fiber direction to expand the visible light image in a second image direction, and the fiber optic bundle further having a transmitting region disposed between the first end and the second end, wherein the first image direction is transverse to the second image direction;

a time delay and integrate sensor disposed in confronting relation with the second end; and a display coupled to the time delay and integrate sensor.

30. The apparatus of claim 29, wherein the first image direction is orthogonal to the second image direction.

31. The apparatus of claim 29, wherein:

the first end defines a first end plane;

the second end defines a second end plane; and the second end plane is oblique with respect to the first end plane.

* * * * *

UNITED STATES PATENT AND TRADEMARK OFFICE
CERTIFICATE OF CORRECTION

PATENT NO. : 6,891,926 B1
DATED : May 10, 2005
INVENTOR(S) : Douglas Raymond Dykaar It is certified that error appears in the above-identified patent and that said Letters Patent is hereby corrected as shown below:

Column 9,
Line 3, "An apparatus of claim 1 comprising" should read -- An apparatus comprising --.

Signed and Sealed this

Thirtieth Day of August, 2005

JON W. DUDAS
*Director of the United States Patent and Trademark Office*